US009988370B2

(12) United States Patent
Numata et al.

(10) Patent No.: US 9,988,370 B2
(45) Date of Patent: Jun. 5, 2018

(54) BENZISOXAZOLE DERIVATIVE SALT

(71) Applicant: RaQualia Pharma Inc., Aichi (JP)

(72) Inventors: Toyoharu Numata, Aichi (JP); Masaki Sudo, Aichi (JP); Xufeng Sun, Schenectady, NY (US)

(73) Assignee: RaQualia Pharma Inc., Aichi (JP)

( * ) Notice: Subject to any disclaimer, the term of this patent is extended or adjusted under 35 U.S.C. 154(b) by 0 days. days.

(21) Appl. No.: 15/312,440

(22) PCT Filed: May 20, 2015

(86) PCT No.: PCT/JP2015/002528
§ 371 (c)(1),
(2) Date: Nov. 18, 2016

(87) PCT Pub. No.: WO2015/178020
PCT Pub. Date: Nov. 26, 2015

(65) Prior Publication Data
US 2017/0081318 A1    Mar. 23, 2017

Related U.S. Application Data

(60) Provisional application No. 62/000,687, filed on May 20, 2014.

(51) Int. Cl.
*C07D 413/14* (2006.01)
*A61K 31/454* (2006.01)

(52) U.S. Cl.
CPC .......... *C07D 413/14* (2013.01); *A61K 31/454* (2013.01)

(58) Field of Classification Search
CPC ............................ C07D 413/14; A61K 31/454
See application file for complete search history.

(56) References Cited

U.S. PATENT DOCUMENTS 6,106,864 A    8/2000  Dolan et al.

FOREIGN PATENT DOCUMENTS

| WO | 91/11172 A1 | 8/1991 |
| WO | 94/02518 A1 | 2/1994 |
| WO | 98/55148 A1 | 12/1998 |
| WO | 00/35298 A1 | 6/2000 |
| WO | 2006/090224 A1 | 8/2006 |
| WO | 2011/101774 A1 | 8/2011 |
| WO | 2012/127878 A1 | 9/2012 |
| WO | 2012/157288 A1 | 11/2012 |

OTHER PUBLICATIONS

Tesseur, I., "Chronic 5-HT 4 receptor activation decreases Aβ production and deposition in hAPP/PS1 mice." Neurobiology of aging 34.7 (2013): 1779-1789.*
Stedman's Medical Dictionary 2017; accessed online May 21, 2017 http://www.stedmansonline.com/popup.aspx?aid=5180022.*
International Search Report issued in PCT/JP2015/002528, dated Jun. 16, 2015 (3 pages).
Written Opinion of the International Searching Authority issued in PCT/JP2015/002528, dated Jun. 16, 2015 (5 pages).
International Preliminary Report on Patentability from PCT/JP2015/002528, dated Jun. 16, 2015 (12 pages).
Bockaert, J. et al.; "The 5-HT4 receptor: a place in the sun"; TiPS, vol. 13, Apr. 1992, pp. 141-145 (5 pages).
Gullikson, G.W. et al.; "Gastrointestinal Motility Responses to the S and R Enantiomers of Zacopride, a 5-HT4 Agonist and 5-HT3 Antagonist"; Drug Development Research, vol. 26, 1992, pp. 405-417 (13 pages).
Eglen, R.M. et al.; "Central 5-HT4 receptors"; Elsevier Science Ltd., vol. 16, Nov. 1995, pp. 391-398 (8 pages).
Bockaert, J. et al.; "5-HT4 Receptors: Potential Therapeutic Implications in Neurology and Psychiatry"; CNS Drugs, vol. 1, 1994, pp. 6-15 (10 pages).
Romanelli, M.N. et al.; "Synthesis and Biological Activity of a Series of Arly Tropanyl Esters and Amides Chemically Related to 1 H-Indole-3-carboxylic Acid endo 8-Methyl-8-azabicyclo [3.2.1] oct-3-yl Ester"; Arzneim Forsch/Drug Res., vol. 43, 1993, pp. 913-918 (6 pages).
Kaumann, A.J. et al.; "A 5-HT4-like receptor in human right atrium"; Naunyn-Schmiedeberg's Arch Pharmacol, vol. 344, 1991, pp. 150-159 (10 pages).
Remington's Pharmaceutical Sciences, 19th Edition, Mack Publishing Company; 1995 (11 pages).
Liang, A.C. et al.; "Fast-dissolving intraoral drug delivery systems"; Expert Opinion in Therapeutic Patents, vol. 11, No. 6, 2001, pp. 981-986 (6 pages).
Lieberman, H. et al; Tablets, vol. 1, Marcel Dekker, New York, 1980, (5 pages).
Verma, R.K. et al.; "Current Status of Drug Delivery Technologies and Future Directions"; Pharmaceutical Technology On-Line, vol. 25, No. 2, 2001, pp. 1-14 (14 pages).
Finnin, B.C. et al.; "Transdermal Penetration Enhancers: Applications, Limitations, and Potential"; Journal of Pharmaceutical Sciences, vol. 88, No. 10, Oct. 1999, pp. 955-958 (4 pages).
Evrard, B. et al.; "Cyclodextrins as a potential carrier in drug nebulization"; Journal of Controlled Release, vol. 96, 2004, pp. 403-410 (8 pages).
Byrn, S.R. et al.; Solid-State Chemistry of Drugs, Second Edition, SSCI, Inc., 1999, pp. 3-43 and 461-503 (85 pages).
Ford, A. et al.; "The 5-HT4 Receptor"; Medicinal Research Reviews, vol. 13, No. 6, 1993, pp. 633-662 (30 pages).
(Continued)

*Primary Examiner* — John M Mauro
(74) *Attorney, Agent, or Firm* — Osha Liang LLP

(57) ABSTRACT

Salts of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid are disclosed. More particularly, salt forms (HCl-salt, HBr-salt, p-toluenesulfonate salt and ethanedisulfonate salt) are disclosed. Furthermore, processes for the preparation of such salt forms, compositions containing such salt forms, and uses of such salt forms are disclosed. A method of treating disease conditions mediated by 5-HT4 receptor activity includes administering an effective amount of such salt forms to an animal, including a human, in need of such treatment.

20 Claims, 5 Drawing Sheets

(56) References Cited

OTHER PUBLICATIONS

Extended European Search Report issued in corresponding European Application No. 15796887.6, dated Nov. 29, 2017 (8 pages).
Caira, Mino R.; "Crystalline Polymorphism of Organic Compounds;" Topics in Current Chemistry; vol. 198; Berlin Heidelberg; 1998 (46 pages).
Gould, Philip L.; "Salt selection for basic drugs;" International Journal of Pharmaceutics, vol. 33, No. 1-3, pp. 201-217; Elsevier; Amsterdam, NL; 1986 (17 pages).

* cited by examiner

{Fig. 1}
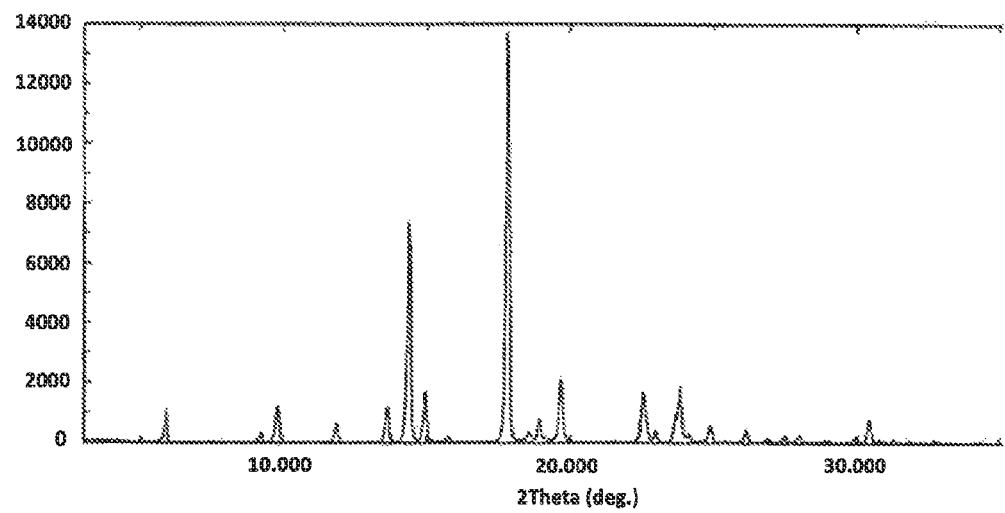
{Fig. 2}
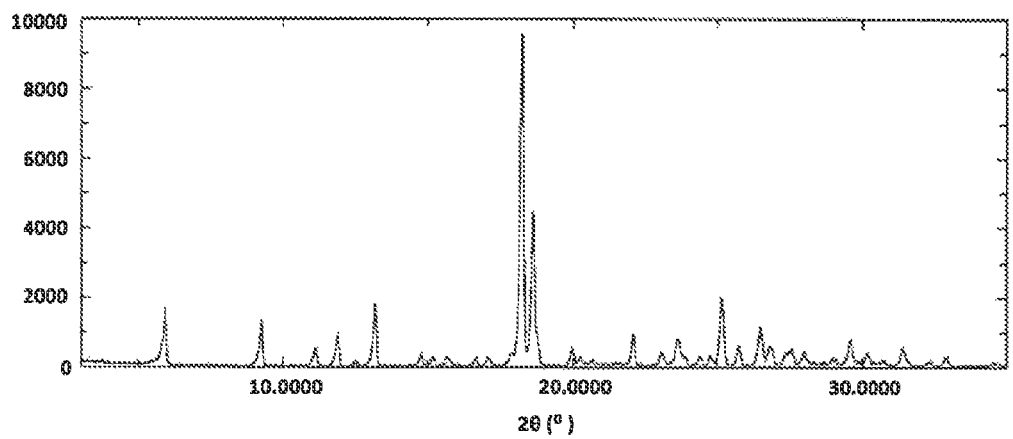

{Fig. 3}
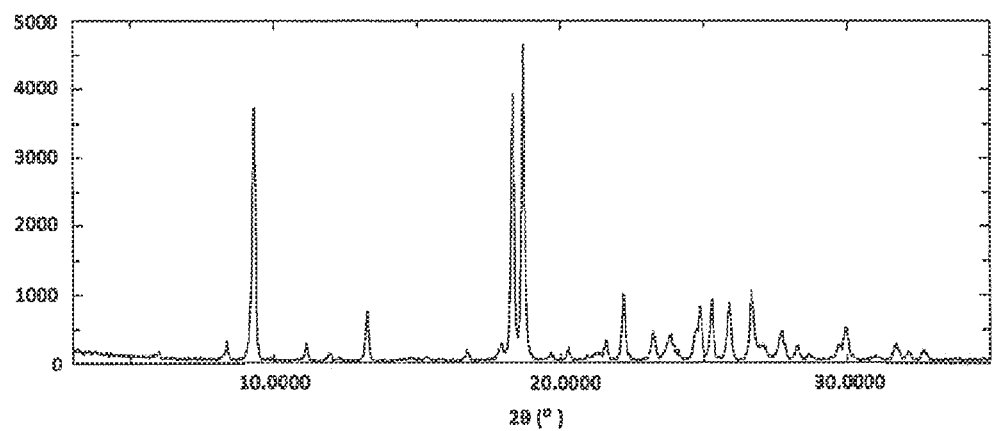
{Fig. 4}
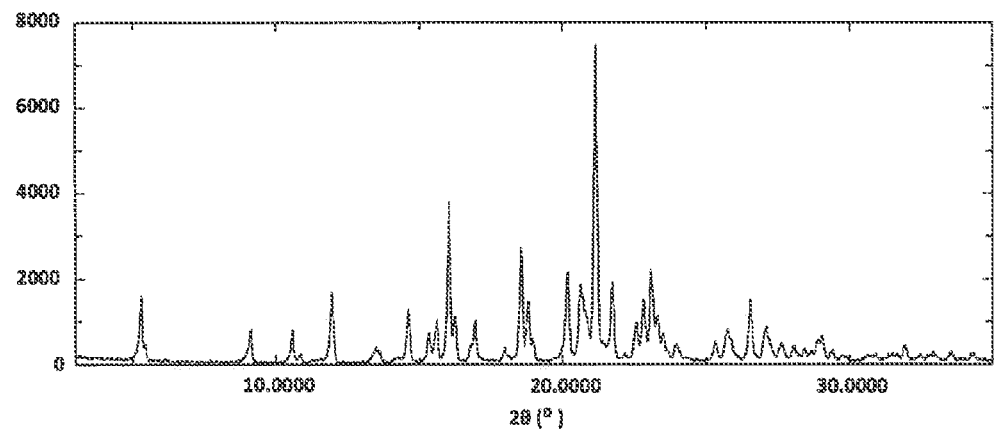

{Fig. 5}
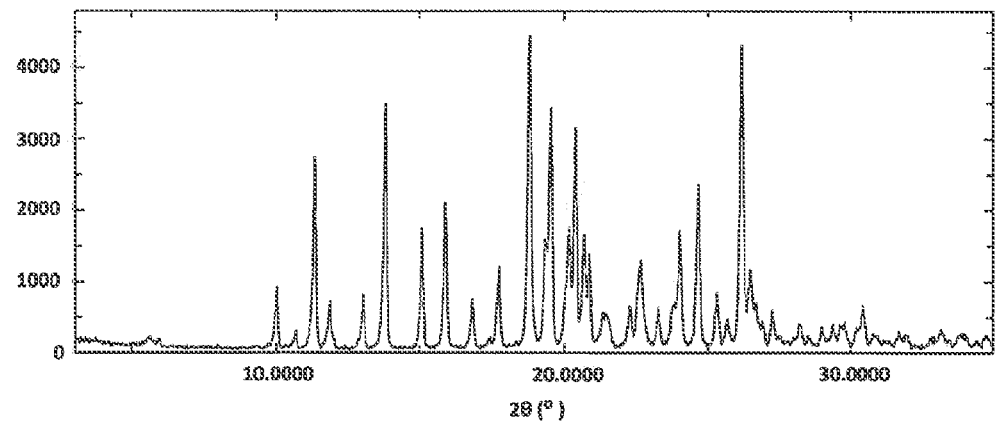
{Fig. 6}
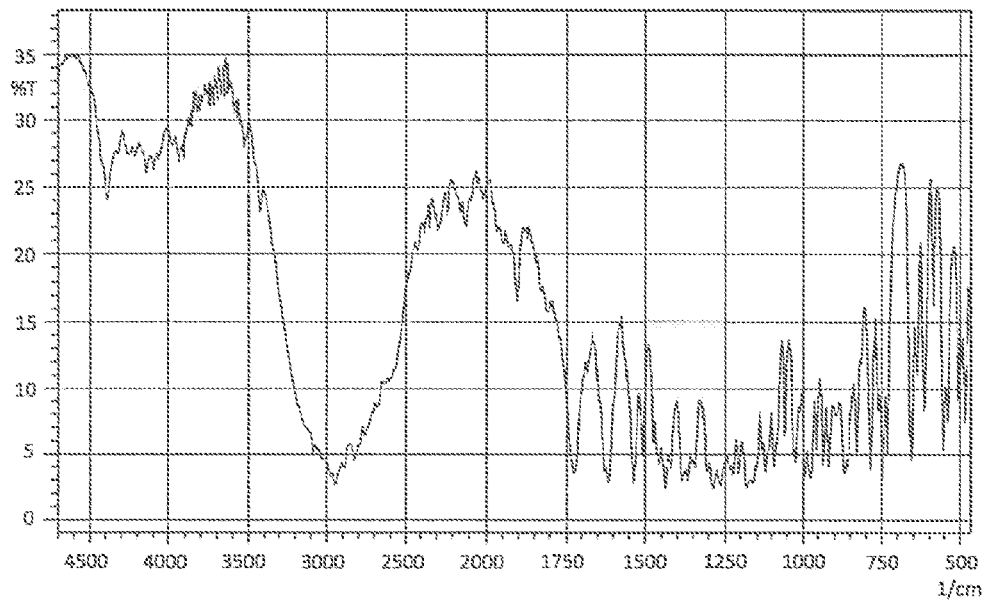

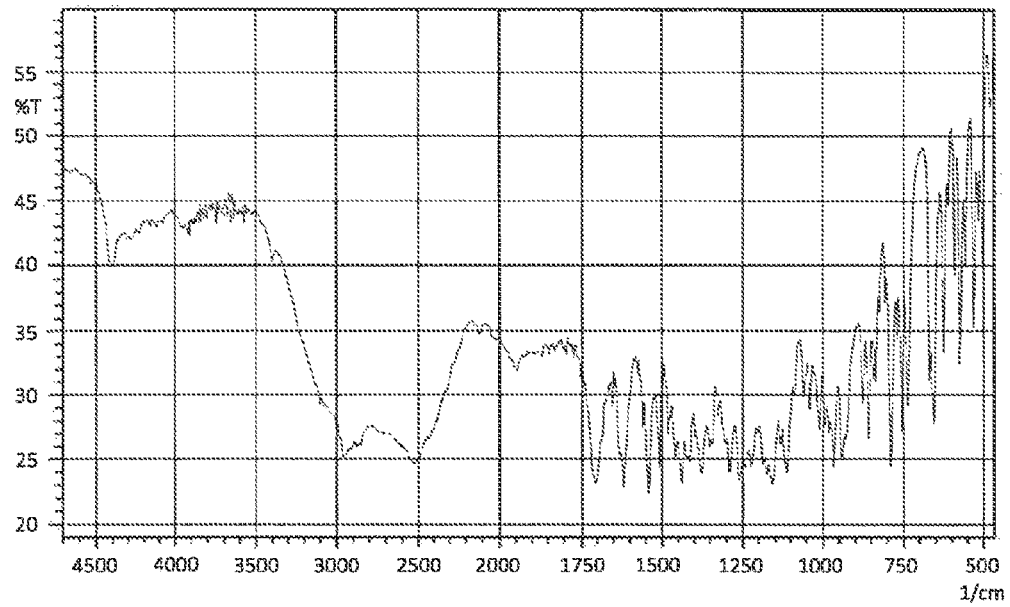
{Fig. 7}
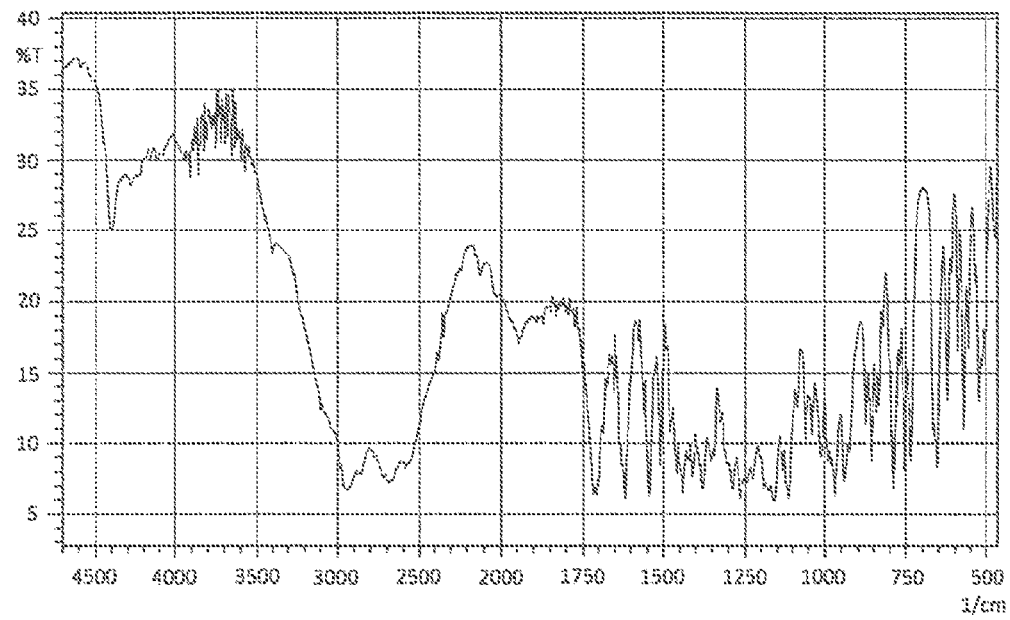
{Fig. 8}

{Fig. 9}
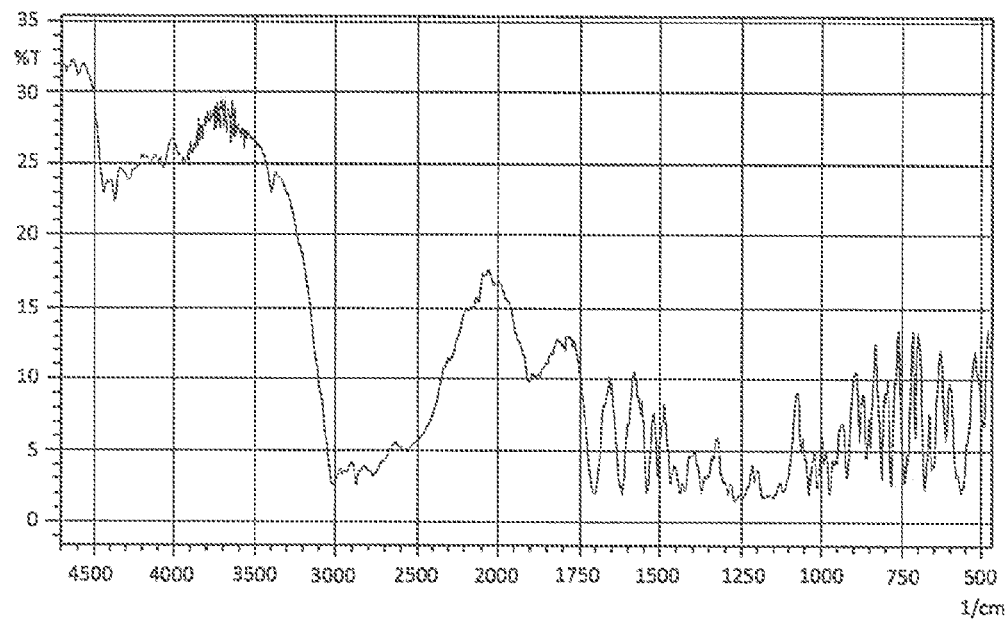
{Fig. 10}
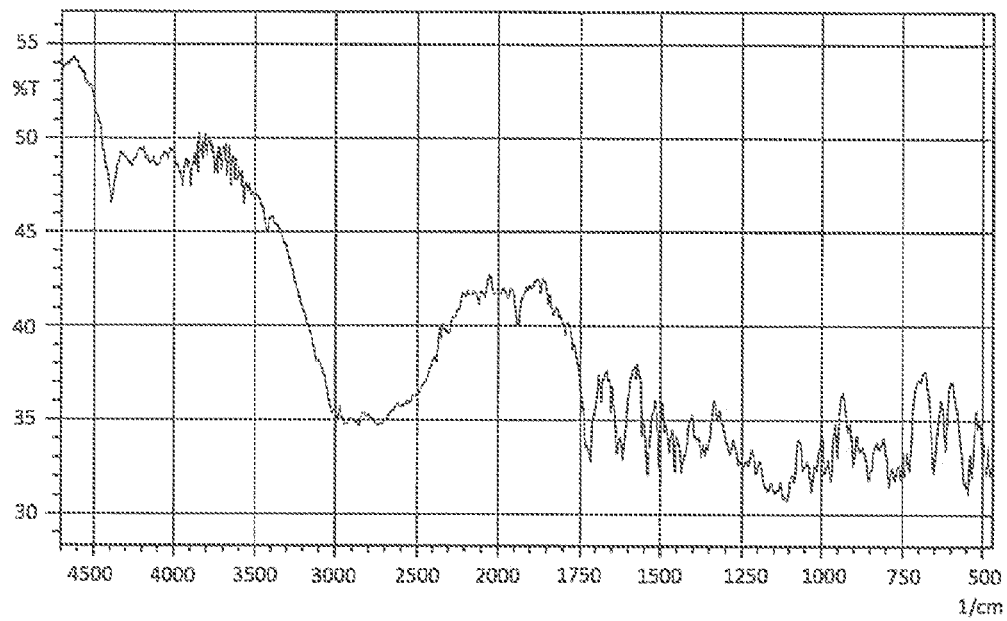

BENZISOXAZOLE DERIVATIVE SALT

TECHNICAL FIELD

One or more embodiments of the present invention relate to novel salts of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid, which may be called Compound A through the present specification. More particularly, one or more embodiments of the invention relate to hydrochloride (HCl-salt), hydrobromide (HBr-salt), p-toluenesulfonate salt (pTSA-salt) and ethanedisulfonate salt (EDSA-salt). One or more embodiments of the invention also relate to processes for the preparation of the salts, compositions containing the salts, and uses of the salts.

BACKGROUND

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid is disclosed in PL1 as a 5-HT4 receptor agonist, which is useful in the treatment or alleviation of disease conditions mediated by 5-HT4 receptor activity; in particular 5-HT4 receptor agonistic activity, such as gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome (See NPL 1 to 13 and PL 2 to 7).

Simply an white solid has been produced in the previously known methods of preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid, described in PL 1. A generic disclosure of pharmaceutically-acceptable salts of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid of the instant application is disclosed, and the free base of the compound of the instant invention is disclosed and claimed, in PL 1 having an international filing date of Dec. 6, 2006, assigned to the assignee hereof. Thus any salts of the compound have been neither pacifically described nor synthesized in prior art.

It has been found that HCl-salt, HBr-salt, pTSA-salt and EDSA-salt of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid shown below, can be isolated as a crystalline form which has advantageous properties such as ease of making a formulation, high solubility, and good stability. In addition, the salts of the present disclosure are more easily purified than a non-crystalline form disclosed in PL 1 (WO2006/090224) and crystalline form disclosed in PL 3 (WO2012/157288).

CITATION LIST

Patent Literature

{PL 1} WO2006/090224.
{PL 2} U.S. Pat. No. 6,106,864.
{PL 3} WO2012/157288
{PL 4} WO00/35298.
{PL 5} WO91/11172.
{PL 6} WO94/02518.
{PL 7} WO98/55148.

Non Patent Literature

{NPL 1} Bockaert J. et al., TiPs 13; 141-145, 1992.
{NPL 2} Ford A. Petal., Med. Res. Rev. 13: 633-662, 1993.
{NPL 3} Gullikson G. W. et al., Drug Dev. Res. 26; 405-417, 1992.
{NPL 4} Richard M. Eglen et al., TiPs 16; 391-398, 1995.
{NPL 5} Bockaert J. et al., CNS Drugs 1; 6-15, 1994.
{NPL 6} Romanelli M. N. et al., Arzheim Forsch./Drug Res., 43; 913-918, 1993.
{NPL 7} Kaumann A. J. et al., Naunyn-Schmiedebergs Arch Pharmacol., 344; 150-159, 1991.
{NPL 8} Remington's Pharmaceutical Sciences, 19th Edition (Mack Publishing Company, 1995).
{NPL 9} Expert Opinion in Therapeutic Patents, H (6), 981-986, by Liang and Chen (2001).
{NPL 10} Tablets, Vol. 1, by H. Lieberman and L. Lachman (Marcel Dekker, New York, 1980).
{NPL 11} Pharmaceutical Technology On-line, 25(2), 1-14, by Verma et al. (2001).
{NPL 12} J Pharm Sci, 88 (10), 955-958, by Finnin and Morgan (October 1999).
{NPL 13} Evrard, B., et al., Journal of Controlled Release 96 (3), pp. 403-410, 2004.
{NPL 14} Byrn S. R. et al., Solid-State Chemistry of Drugs 2nd ed., pp 3-43 and 461-503, 1999, SSCI, Inc.

SUMMARY

As well-known by skilled in the art, it has been a desirable goal to find or to prepare a salt form in drug development from the various viewpoints including formulation and manufacturing of the drug. This is the most widely used approach to increase solubility of weakly acidic or basic NCEs (new chemical entities). (see e.g. Wadke, D. A. et al, Pharmaceutical Dosage Forms: Tablets, Vol. 1, 1989, pp 1-73). The advantages of a salt are typically driven by the counter ion and selection of counter-ion is based on many parameters such as solubility, hygroscopicity and stability of the physical form. In spite of the numerous advantages associated with salt forms, developing a stable salt is not always feasible. In many cases, increased dissolution rate is difficult to achieve because of the reconversion of salts into their respective acid or base forms.

According to the line, great efforts have been made to find or prepare a salt form of 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid since the said compound was disclosed in 2006 (WO2006/090224), but no pharmaceutically suitable salt forms of the said compound have been identified yet.

As disclosed in the working example of the present invention, a white solid of the said compound is dissolved in n-BuOH at 70° C. and to which conc. HCl (37 wt %, 35.5 microL, 0.425 mmol) is added. The mixture is stirred at 70° C. overnight, then gradually cooled down to room temperature. Resulting precipitates are collected by filtration, washed with EtOH and dried in vacuo to give the HCl-salt.

As disclosed in the working example of the present invention, a white solid of the said compound is dissolved in n-BuOH at 65° C. and to which EtOH solution of HBr is added. The mixture is stirred at 65° C. overnight, then gradually cooled down to room temperature. Resulting precipitates are collected by filtration, washed with EtOH and dried in vacuo to give the HBr-salt.

As disclosed in the working example of the present invention, a white solid of the said compound is dissolved in n-BuOH at 65° C. and to which a solution of p-toluenesulfonic acid monohydrate in CH₃CN is added. The mixture is stirred at 65° C. for 3 min, then gradually cooled down to room temperature. Resulting precipitates are collected by filtration, washed with AcOEt and dried in vacuo to give the pTSA-salt.

As disclosed in the working example of the present invention, a white solid of the said compound is dissolved in n-BuOH at 65° C. and to which a solution of ethanedisulfonic acid dihydrate in EtOH is added. The mixture is stirred at 65° C. for 3 min, then gradually cooled down to room temperature. Resulting precipitates are filtered, washed with AcOEt and dried in vacuo to give the EDSA-salt.

Various salts including, phosphoric acid salt, sulfuric acid salt, methanesulfonic acid salt, ethanesulfonic acid salt, benzenesulfonic acid salt, (+)-(1S)-camphor-10-sulfonic acid salt, napthalene-2-sulfonic acid salt, naphthalene-1,5-disulfonic acid salt, maleic acid salt, sodium salt, potassium salt, calcium salt, magnesium salt, zinc salt, betaine salt, choline salt, diethylamine salt, piperazine salt and benzathine salt other than the HCl-salt, the HBr-salt, the pTSA-salt, and the EDSA-salt are prepared in the following manner. Namely a white solid of the said compound is dissolved in an appropriate solvent which includes EtOH, n-BuOH, AcOEt, MEK, CH₃CN or THF at 55° C. to 70° C. and to which a solution of the counterion source in an appropriate solvent which includes MeOH, EtOH, i-PrOH, dioxane and/or water is added. The mixture is stirred at room temperature to reflux temperature of the solvent, preferably at 55° C. to 70° C., for 3 min to overnight, then gradually cooled down to room temperature. Resulting precipitates are collected by filtration, washed with an appropriate solvent which includes EtOH, n-BuOH, AcOEt, MEK, CH₃CN or THF, and dried in vacuo to give the corresponding salt.

However, oils are obtained from some experiments such as benzenesulfonic acid in both EtOH and CH₃CN, pTSA in EtOH and zinc acetate in EtOH.

Only the free compound is recovered from some experiments such as (+)-(1S)-camphor-10-sulfonic acid in both EtOH and AcOEt, napthalene-2-sulfonic acid in both EtOH and AcOEt, sodium acetate in CH₃CN, betaine in MEK and diethylamine in both n-BuOH and CH₃CN.

Solids are obtained from some experiments such as sulfuric acid in both n-BuOH and MEK, phosphoric acid salt in both n-BuOH and CH₃CN, sodium hydroxide in both EtOH and CH₃CN and potassium acetate in n-BuOH and MEK. However, they are not practically useful as a pharmaceutical acceptable salt. In addition, once the seed of the salt is obtained, where applicable, the same salt can generally be easily obtained in a small scale synthesis. On large scale synthesis, temperature control is essential for preparing a pharmaceutically suitable salt.

One or more embodiments of the present invention provide pharmaceutically suitable salt of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid, which can be easily, economically and reproducibly prepared for use in a pharmaceutical formulation having consistent performance characteristics, which are excellent in for example stability and non-hygroscopicity. Also, one or more embodiments of the present invention provide processes for the preparation of compositions containing such salt and to provide uses of such salt.

Thus, one or more embodiments of the invention provides:

[1]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt, which is characterized by a powder X-ray diffraction (PXRD) pattern obtained by irradiation with Cu-K-alpha radiation which includes main peaks at 2-theta 5.9, 9.4, 11.1, 11.9, 13.2, 18.2, 18.6, 22.1, 25.2 and 26.5 (°), wherein each peak has a margin of error of +/−0.2 (°);

[2]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt, which is characterized by an infrared (IR) spectrum (diffuse reflection) which shows absorption bands at 4392, 3393, 2953, 2517, 1942, 1705, 1618, 1541, 1508, 1439, 1377, 1288, 1261, 1223, 1155, 1111, 1059, 1040, 1011, 966, 941, 878, 856, 787, 754, 733, 654, 625, 590, 573, 557, 529, 503, and 478 cm⁻¹, wherein each peak has a margin of error of +/−2 cm⁻¹;

[3]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt as described in [1] or [2], which is further characterized by differential scanning calorimetry (DSC) in which it exhibits an endothermic event at 232° C., wherein the temperature has a margin of error of +/−1° C.;

[4]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt, which is characterized by a powder X-ray diffraction (PXRD) pattern obtained by irradiation with Cu-K-alpha radiation which includes main peaks at 2-theta 9.4, 13.3, 18.4, 18.7, 22.2, 23.2, 23.8, 24.8, 25.2, 25.9 and 26.6 (°), wherein each peak has a margin of error of +/−0.2 (°);

[5]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt, which is characterized by an infrared (IR) spectrum (diffuse reflection) which shows absorption bands at 4405, 3397, 2941, 2693, 2122, 1942, 1717, 1618, 1545, 1508, 1441, 1410, 1377, 1352, 1287, 1261, 1225, 1157, 1111, 1059, 1040, 1011, 968, 941, 874, 856, 787, 754, 735, 652, 621, 590, 571, 557, 525, 503 and 478 cm⁻¹, wherein each peak has a margin of error of +/−2 cm⁻¹;

[6]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt as described in [4] or [5], which is further characterized by differential scanning calorimetry (DSC) in which it exhibits an endothermic event at 256° C., wherein the temperature has a margin of error of +/−1° C.;

[7]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt, which is characterized by a powder X-ray diffraction (PXRD) pattern obtained by irradiation with Cu-K-alpha radiation which includes main peaks at 2-theta 5.3, 11.9, 14.6, 16.0, 18.5, 18.7, 20.1, 20.6, 21.1, 22.7 and 23.0 (°), wherein each peak has a margin of error of +/−0.2 (°);

[8]
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt, which is characterized by an infrared (IR) spectrum (diffuse reflection) which shows absorption bands at 4438, 4369, 3397, 3017, 2868, 2768, 1902, 1701, 1616, 1541, 1508, 1466, 1436, 1422, 1371, 1290, 1267, 1206, 1180, 1150, 1117, 1038, 1013, 972, 918, 881, 860, 847, 812, 783, 738, 708, 677, 650, 611, 565 and 492 cm$^{-1}$, wherein each peak has a margin of error of +/−2 cm$^{-1}$;

[9]

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt as described in [7] or [8], which is further characterized by differential scanning calorimetry (DSC) in which it exhibits an endothermic event at 207° C., wherein the temperature has a margin of error of +/−1° C.;

[10]

4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid EDSA-salt, which is characterized by a powder X-ray diffraction (PXRD) pattern obtained by irradiation with Cu-K-alpha radiation which includes main peaks at 2-theta 11.3, 13.8, 15.1, 15.9, 18.8, 19.5, 20.2, 20.4, 20.7, 24.0, 24.7 and 26.2)(°, wherein each peak has a margin of error of +/−0.2 (°);

[11]

4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid EDSA-salt, which is characterized by an infrared (IR) spectrum (diffuse reflection) which shows absorption bands at 4388, 3948, 3422, 2741, 1937, 1717, 1616, 1539, 1506, 1435, 1373, 1285, 1244, 1204, 1169, 1146, 1107, 1030, 989, 972, 951, 901, 854, 789, 772, 756, 741, 729, 652, 615, 546, 532 and 490 cm$^{-1}$, wherein each peak has a margin of error of +/−2 cm$^{-1}$;

[12]

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt as described in [10] or [11], which is further characterized by differential scanning calorimetry (DSC) in which it exhibits an endothermic event at 246° C., wherein the temperature has a margin of error of +/−1° C.;

[13]

A pharmaceutical composition including 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid salt form as described in any one of [1] to [12], together with one or more pharmaceutically acceptable excipients;

[14]

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salt as described in any one of [1] to [12] for use as a medicament;

[15]

A use of 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid salt form as described in any one of [1] to [12], or a pharmaceutical composition as described in [13], in the preparation of a medicament for the curative, palliative or prophylactic treatment of disease conditions mediated by 5-HT4 receptor activity;

[16]

A method of treating disease conditions mediated by 5-HT4 receptor activity, which comprises administering an effective amount of 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid salt form as described in any one of [1] to [12], or a pharmaceutical composition as described in [13], to an animal, including a human, in need of such treatment;

[17]

A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt as described in any one of [1] to [3], comprising the step of exposing the compound with HCl;

[18]

A process for preparing 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid HBr-salt as described in any one of [4] to [6], comprising the step of exposing the compound with HBr;

[19]

A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt as described in any one of [7] to [9], comprising the step of exposing the compound with p-toluenesulfonic acid;

[20]

A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt as described in any one of [10] to [12], comprising the step of exposing the compound with ethanedisulfonic acid.

As mentioned above, one or more embodiments of the present invention find or prepare a salt form in drug development from the various viewpoints including formulation and manufacturing of the drug. Specifically, one or more embodiments of the present disclosure provide salt forms of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid known as the HCl-salt, the HBr-salt, the pTSA-salt, and the EDSA-salt. 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid may be abbreviated as the said compound throughout the specification.

No pharmaceutically suitable salt forms of the said compound other than the above salts have been identified in spite of great efforts of those skilled in the art.

Free form of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid is disclosed in WO2006/090224 as a white powder and is also disclosed in WO2012/157288 as Polymorph Form I and Polymorph Form II.

All of the salts as described herein have an excellent and unexpected advantage over the free forms disclosed in the prior art, WO2006/090224 and WO2012/157288. The HCl-salt, the HBr-salt, the pTSA-salt, and the EDSA-salt are found to be more stable than the free forms known to the public.

In addition, in terms of hygroscopicity, the salts as described herein have an excellent and unexpected advantage over the free forms of the compound disclosed in the prior art.

As mentioned above, the HCl-salt, the HBr-salt, the pTSA-salt, and the EDSA-salt have a good solid-state stability as water uptake after 5 days comparing with the free forms disclosed in the prior art, and particularly, the HBr-salt and the pTSA-salt are preferable in the solid-state stability.

As mentioned above, the HCl-salt, the HBr-salt, the pTSA-salt, and the EDSA-salt have a good solid-state stability under 40° C./75% RH comparing with the free forms disclosed in the prior art, and particularly, the HBr-salt, the pTSA-salt, and the EDSA-salt are preferable in the solid-state stability.

The HCl-salt, the HBr-salt, the pTSA-salt, and the EDSA-salt as described herein are found to be applicable for a large scale synthesis. They have acceptable solid-state properties for solid-dosage form development.

BRIEF DESCRIPTION OF DRAWINGS

FIG. 1 shows the PXRD pattern of Polymorph Form I obtained from the method of preparing 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid described in Example 2 of FIG. 2 shows the PXRD pattern of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt.

FIG. 3 shows the PXRD pattern of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt.

FIG. 4 shows the PXRD pattern of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt.

FIG. 5 shows the PXRD pattern of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt.

FIG. 6 shows the IR spectra (diffuse reflection) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid Polymorph Form I.

FIG. 7 shows the IR spectra (diffuse reflection) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt.

FIG. 8 shows the IR spectra (diffuse reflection) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt.

FIG. 9 shows the IR spectra (diffuse reflection) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt.

FIG. 10 shows the IR spectra (diffuse reflection) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt.

DESCRIPTION OF EMBODIMENTS

Accordingly, one or more embodiments of the present invention provides 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt, which is characterized by a powder X-ray diffraction (PXRD) pattern obtained by irradiation with Cu-K-alpha radiation which includes main peaks at 2-theta 5.9, 9.4, 11.1, 11.9, 13.2, 18.2, 18.6, 22.1, 25.2 and 26.5 (°), wherein each peak has a margin of error of +/−0.2 (°);

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt, which is characterized by an infrared (IR) spectrum (diffuse reflection) which shows absorption bands at 4392, 3393, 2953, 2517, 1942, 1705, 1618, 1541, 1508, 1439, 1377, 1288, 1261, 1223, 1155, 1111, 1059, 1040, 1011, 966, 941, 878, 856, 787, 754, 733, 654, 625, 590, 573, 557, 529, 503, and 478 cm$^{-1}$, wherein each peak has a margin of error of +/−2 cm$^{-1}$;

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt as described in [1] or [2], which is further characterized by differential scanning calorimetry (DSC) in which it exhibits an endothermic event at 232° C., wherein the temperature has a margin of error of +/−1° C.;

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt, which is characterized by a powder X-ray diffraction (PXRD) pattern obtained by irradiation with Cu-K-alpha radiation which includes main peaks at 2-theta 9.4, 13.3, 18.4, 18.7, 22.2, 23.2, 23.8, 24.8, 25.2, 25.9 and 26.6 (°), wherein each peak has a margin of error of +/−0.2 (°);

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt, which is characterized by an infrared (IR) spectrum (diffuse reflection) which shows absorption bands at 4405, 3397, 2941, 2693, 2122, 1942, 1717, 1618, 1545, 1508, 1441, 1410, 1377, 1352, 1287, 1261, 1225, 1157, 1111, 1059, 1040, 1011, 968, 941, 874, 856, 787, 754, 735, 652, 621, 590, 571, 557, 525, 503 and 478 cm$^{-1}$, wherein each peak has a margin of error of +/−2 cm$^{-1}$;

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt as described above, which is further characterized by differential scanning calorimetry (DSC) in which it exhibits an endothermic event at 256° C., wherein the temperature has a margin of error of +/−1° C.;

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt, which is characterized by a powder X-ray diffraction (PXRD) pattern obtained by irradiation with Cu-K-alpha radiation which includes main peaks at 2-theta 5.3, 11.9, 14.6, 16.0, 18.5, 18.7, 20.1, 20.6, 21.1, 22.7 and 23.0 (°), wherein each peak has a margin of error of +/−0.2 (°);

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt, which is characterized by an infrared (IR) spectrum (diffuse reflection) which shows absorption bands at 4438, 4369, 3397, 3017, 2868, 2768, 1902, 1701, 1616, 1541, 1508, 1466, 1436, 1422, 1371, 1290, 1267, 1206, 1180, 1150, 1117, 1038, 1013, 972, 918, 881, 860, 847, 812, 783, 738, 708, 677, 650, 611, 565 and 492 cm$^{-1}$, wherein each peak has a margin of error of +/−2 cm$^{-1}$;

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt as described above, which is further characterized by differential scanning calorimetry (DSC) in which it exhibits an endothermic event at 207° C., wherein the temperature has a margin of error of +/−1° C.;

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt, which is characterized by a powder X-ray diffraction (PXRD) pattern obtained by irradiation with Cu-K-alpha radiation which includes main peaks at 2-theta 11.3, 13.8, 15.1, 15.9, 18.8, 19.5, 20.2, 20.4, 20.7, 24.0, 24.7 and 26.2 (°), wherein each peak has a margin of error of +/−0.2 (°);

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt, which is characterized by an infrared (IR) spectrum (diffuse reflection) which shows absorption bands at 4388, 3948, 3422, 2741, 1937, 1717, 1616, 1539, 1506, 1435, 1373, 1285, 1244, 1204, 1169, 1146, 1107, 1030, 989, 972, 951, 901, 854, 789, 772, 756, 741, 729, 652, 615, 546, 532 and 490 cm$^{-1}$, wherein each peak has a margin of error of +/−2 cm$^{-1}$; and 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt as described above, which is further characterized by differential scanning calorimetry (DSC) in which it exhibits an endothermic event at 246° C., wherein the temperature has a margin of error of +/−1° C.

In one embodiment of the present invention, there is provided a pharmaceutical composition including 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salt form of the present invention, together with one or more pharmaceutically acceptable excipients;

One or more embodiments of the present invention, provide 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salt form of the present invention for use as a medicament.

In yet another embodiment of the present invention, there is provided the use of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salt form of the present invention in the manufacture of a medicament for the treatment of any disease which mediated by a 5-HT4 receptor activity, particularly for the curative, prophylactic or palliative treatment of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome.

As an alternative aspect, there is provided a method for the treatment of any disease which mediated by a 5-HT4 receptor activity, particularly for the curative, prophylactic or palliative treatment of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome, including administration of a therapeutically effective amount of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salt form of the present invention to an animal, including a human, in need of such treatment.

The 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid salt form as described herein is useful for the general treatment of disease conditions mediated by 5-HT4 receptor activity.

The 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid salt form as described herein can also be useful for the treatment of a disorder or condition selected from the group consisting of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome.

Synthetic routes for the preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid free form are described in WO2006/090224 and in WO2012/157288.

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt can be prepared by exposing the compound with HCl solution.

Depending on the concentration of the compound, the reducing rate of temperature at the crystallization is generally lower than 70° C./hour at the concentration of about 0.1 mg/mL to about 200 mg/mL. Preferably lower than 50° C./hour, more preferably lower than 20° C./hour, and most preferably lower than 5° C./hour can be applied for the crystallization.

Preferable solvent for the salt preparation includes EtOH, n-BuOH, MEK, or CH$_3$CN, and more preferably n-BuOH and MEK.

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt can be prepared by exposing the compound with HBr solution.

Depending on the concentration of the compound, the reducing rate of temperature at the crystallization is generally lower than 65° C./hour at the concentration of about 0.1 mg/mL to about 200 mg/mL. Preferably lower than 50° C./hour, more preferably lower than 20° C./hour, and most preferably lower than 5° C./hour can be applied for the crystallization.

Preferable solvent for the salt preparation includes EtOH, AcOEt, MEK, CH$_3$CN or THF, and more preferably n-BuOH, AcOEt and MEK.

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt can be prepared by exposing the compound with p-toluenesulfonic acid solution.

Depending on the concentration of the compound, the reducing rate of temperature at the crystallization is generally lower than 65° C./hour at the concentration of about 0.1 mg/mL to about 200 mg/mL. Preferably lower than 50° C./hour, more preferably lower than 20° C./hour, and most preferably lower than 5° C./hour can be applied for the crystallization.

Preferable solvent for the salt preparation includes AcOEt.

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt can be prepared by exposing the compound with ethanedisulfonic acid solution.

Depending on the concentration of the compound, the reducing rate of temperature at the crystallization is generally lower than 65° C./hour at the concentration of about 0.1 mg/mL to about 200 mg/mL. Preferably lower than 50° C./hour, more preferably lower than 20° C./hour, and most preferably lower than 5° C./hour can be applied for the crystallization.

Preferable solvent for the salt preparation includes n-BuOH or AcOEt.

The 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid salt form as described herein can be administered alone or in combination with one or more other drugs (or as any combination thereof). Generally, they will be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Thus, in one or more embodiments of the present invention, there is provided a pharmaceutical composition including 4-{[4-({[4-(2,2,2-trifluoroethoxy)-1,2-benzisoxazol-3-yl]oxy}methyl)-piperidin-1-yl]methyl}tetrahydro-2H-pyran-4-carboxylic acid salt form and one or more suitable excipients. The composition is suitable for the treatment of disease conditions mediated by 5-HT4 receptor activity.

The term "salt form(s)", as used herein, includes HCl-salt, HBr-salt, pTSA-salt, and/or EDSA-salt.

Weight purity of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salt form as described herein is not limited, but an essentially pure salt form may be used for specific embodiments of this invention.

References herein to "treatment" include references to curative, palliative and prophylactic treatment.

For non-human animal administration, the term 'pharmaceutical' as used herein may be replaced by 'veterinary.'

Pharmaceutical compositions suitable for the delivery of the salt form as described herein and methods for the preparation will be readily apparent to those skilled in the art. Such compositions and methods for the preparation may be found, for example, in Remington's Pharmaceutical Sciences, 19th Edition (Mack Publishing Company, 1995).

Oral Administration

The salt form as described herein may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal or mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid taken from a sachet etc.

The salt form as described herein may also be used in fast-dissolving, fast-disintegrating dosage forms such as those described in Wermuth, C. G. and Stahl, P. H. (Eds.), Handbook of Pharmaceutical Salts: Properties, Selection, and Use, PP 19-39 and 83-116, Wiley-Verlag Helvetica Acta, (2002).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant comprises from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may be contained from 0.2 weight % to 5 weight % of the tablet, and glidants may be contained from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a salt form in accordance with one or more embodiments of the invention, a film-forming polymer, a binder, a solvent, a humectant, a plasticizer, a stabilizer or emulsifier, a viscosity-modifying agent and a solvent. Some components of the formulation may perform more than one function.

Salt forms as described herein may be water-soluble or insoluble depending upon circumstances or conditions. A water-soluble compound typically may be contained from 1 weight % to 80 weight %, more typically from 20 weight % to 50 weight %, of the solutes. Less soluble compounds may be contained in a greater proportion of the composition, typically up to 88 weight % of the solutes. Alternatively, salt forms as described herein may be in the form of multiparticulate beads.

The film-forming polymer may be selected from natural polysaccharides, proteins, or synthetic hydrocolloids and is typically present in the range of 0.01 to 99 weight %, more typically in the range of 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with one or more embodiments of the invention are typically prepared by evaporative drying of thin aqueous films coated onto a peelable backing support or paper.

This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al. (2001). The use of chewing gum to achieve controlled release is described in WO 00/35298.

Parenteral Administration

The salt form as described herein may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

Formulations for parenteral administration may be formulated to be immediate and/or modified release. Modified release formulations include delayed-, sustained-, pulsed-, controlled-, targeted and programmed release. Thus, in one ore more embodiments of the invention, the salt form may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(lactic-co-glycolic acid) (PLGA) microspheres.

Topical Administration

The salt form as described herein may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject (trade mark), Bioject (trade mark), etc.) injection. Topical administration may also be achieved using a patch, such as a transdermal iontophoretic patch.

Formulations for topical administration may be formulated to be immediate and/or modified release. Modified release formulations include delayed-, sustained-, pulsed-, controlled-, targeted and programmed release.

The salt form as described herein may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of a salt form in accordance with one or more embodiments of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound as described herein, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 micro g to 20 mg of the compound as described herein per actuation and the actuation volume may vary from 1 micro L to 100 micro L. A typical formulation may comprise a salt form in accordance with one or more embodiments of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations as described herein intended for inhaled/intranasal administration.

Formulations for inhaled/intranasal administration may be formulated to be immediate and/or modified release using, for example, PLGA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with one or more embodiments of the invention are typically arranged to administer a metered dose or "puff" containing from 1 microg to 20 mg of the Compound A. The overall daily dose will typically be in the range of 1 microg to 100 mg which may be administered in a single dose or, more usually, as divided doses throughout the day.

Rectal/Intravaginal Administration

The salt form as described herein may be administered rectally or vaginally, for example, in the form of a suppository, pessary, or enema. Cocoa butter is a traditional suppository base, but various alternatives may be used as appropriate.

Formulations of one or more embodiments of the invention for rectal/vaginal administration may be formulated to be immediate and/or modified release. Modified release formulations include delayed-, sustained-, pulsed-, controlled-, targeted and programmed release.

Ocular/Aural Administration

The salt form as described herein may also be administered directly to the eye or ear, typically in the form of drops of a micronized suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gellan gum, may be incorporated together with a preservative, such as benzalkonium chloride. Such formulations may also be delivered by iontophoresis.

Formulations including the salt as described herein for ocular/aural administration may be formulated to be immediate and/or modified release. Modified release formulations include delayed-, sustained-, pulsed-, controlled-, targeted, or programmed release.

Other Technologies

The salt form as described herein may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in International Patent Publication Nos. WO 91/11172, WO 94/02518, WO 98/55148 and Evrard, B., et al., Journal of Controlled Release 96 (3), pp. 403-410, 2004.

Dosage

For treating or preventing the disease conditions mediated by 5-HT4 receptor activity such as gastrointestinal diseases, a suitable dosage level of salt form as described herein is about 0.0001 to 1000 mg per day, preferably about 0.001 to 100 mg per day, and more preferably about 0.005 to 50 mg per day, and most preferably 1 to 50 mg per day of the active compound. The compounds may be administered on a regimen of 1 to 4 times per day. In some cases, however, a dosage outside these limits may be used.

These dosages are based on an average human subject having a weight of about 60 kg to 70 kg. The physician will readily be able to determine doses for subjects whose weight falls outside this range, such as infants and the elderly. For the avoidance of doubt, references herein to "treatment" include references to curative, palliative and prophylactic treatment.

The salt form as described herein (Compound A) may also optionally be combined with another pharmacologically active compound, or with two or more other pharmacologically active compounds, particularly for the treatment of disease conditions mediated by 5-HT4 receptor activity. For example, the salt form as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butalbital, mephobarbital, metharbital, methohexital, pentobarbital, phenobartital, secobarbital, talbutal, thiamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphenadrine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2 (1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6,13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resiniferatoxin) or antagonist (e.g. capsazepine);

a transient receptor potential cation channel subtype (V1, V2, V3, V4, M8, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1 D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJ R-2403), (R)-5-(2-azetidinylmethoxy)-2-chloropyridine (ABT-594) or nicotine;

Tramadol (registered trademark);

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4, 3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d] pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-ypethyl]-4-propoxybenzenesulfonamide;

an alpha-2-delta ligand such as gabapentin, pregabalin, 3-methylgabapentin, (1alpha,3alpha,5alpha)(3-aminomethyl-bicyclo[3.2.0]hept-3-yl)-acetic acid, (3S,5R)-3 am inomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

a metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, bupropion, bupropion metabolite hydroxybupropion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as

S-[2-[(1-iminoethyl)amino]ethyl]-L-homocysteine,

S-[2-[(1-iminoethyl)-amino]ethyl]-4,4-dioxo-L-cysteine,

S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile;

2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl] thio]-5-thiazolebutanol, 2-[[(1R,3S)-3-amino-4-hydroxy-1-(5-thiazolypbutyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;
a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;
a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,
a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);
a sodium channel blocker, such as lidocaine;
a calcium channel blocker, such as ziconotide, zonisamide, mibefradil;
a 5-HT3 antagonist, such as ondansetron;
a chemotherapy drug such as oxaliplatin, 5-fluorouracil, leucovorin, paclitaxel;
a calcitonin gene related peptide (CGRP) antagonist;
a bradykinin (BK1 and BK2) antagonist;
a voltage gated sodium dependent channel blocker ($Na_{v1.3}$, $Na_{v1.8}$);
a voltage dependent calcium channel blocker (N-type, T-type);
a P2X (ion channel type ATP receptor) antagonist;
an acid-sensing ion channel (ASIC1a, ASIC3) antagonist;
an Angiotensin AT2 antagonist;
a Chemokine CCR2B receptor antagonist;
a Cathepsin (B, S, K) inhibitor;
a sigma1 receptor agonist or antagonist;
and the pharmaceutically acceptable salts and solvates thereof.

Such combinations offer significant advantages, including synergistic activity, in therapy.

Combination Drug and Kit

One embodiment of the present invention is a combination of the salt form as described herein, and a drug for gastrointestinal diseases, which is different from the salt form as described herein. A "combination" according to one or more embodiments of the invention may be present as a "fix combination" or as a "kit of parts combination". A "fix combination" is defined as a combination wherein the (i) at least one drug for gastrointestinal diseases, which is different from the salt form as described herein, and (ii) salt form are present in one unit. A "kit of parts combination" is defined as a combination wherein the (i) at least one drug for gastrointestinal diseases, which is different from the salt form as described herein, and (ii) salt form are present in more than one unit. The components of the "kit of parts combination" may be administered simultaneously, sequentially or separately. The molar ratio of the drug for gastrointestinal diseases, which is different from the salt form as described herein, to salt form used according to the invention is within the range of from 1:100 to 100:1, such as from 1:50 to 50:1 or from 1:20 to 20:1 or from 1:10 to 10:1. The two drugs may be administered separately in the same ratio. Examples of acid secretion inhibiting agents are other 5-HT4 agonists, proton pump inhibitors, H2 receptor antagonists, and drugs for IBS or constipations. These examples are H2 blocking agents such as cimetidine, ranitidine; as well as proton pump inhibitors such as pyridinylmethylsulfinyl benzimidazoles such as omeprazole, esomeprazole, lansoprazole, pantoprazole, rabeprazole or related substances such as leminoprazole.

One or more embodiments of the present invention provide a combination comprising 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid salt form and one or more therapeutic agents, such as those listed above, for simultaneous, separate or sequential use in the curative, prophylactic or palliative treatment of disease conditions mediated by 5-HT4 receptor activity.

EXAMPLES

The following examples are for reference only.
Analysis
Nuclear Magnetic Resonance (NMR)
NMR data are determined at 270 MHz (JEOL JNM-LA 270 spectrometer) or 300 MHz (JEOL JNM-LA300 spectrometer) using deuterated dimethylsulfoxide (99.9% D) as solvent, relative to tetramethylsilane (TMS) as internal standard in parts per million (ppm); conventional abbreviations used are: s=singlet, d=doublet, t=triplet, q=quartet, m=multiplet, br=broad, etc.

Powder X-Ray Diffraction (PXRD)
The PXRD analyses are performed using a Rigaku RINT-TTR X-ray powder diffractometer using Cu-K-alpha radiation. The samples can also be measured under the high/low temperature condition by using the attachment of the variant-temperature sample holder. The instrument is equipped with a fine focus X-ray tube. The tube voltage and amperage are set to 50 kV and 300 mA respectively. The divergence and scattering slits are set at 0.5° and the receiving slit is set at 0.15 mm. Diffracted radiation is detected by a NaI scintillation detector. A theta-two theta continuous scan at 4°/min (step size 0.02°) from 3 to 40 2-theta (°) is used. A silicon standard is analyzed to check the machine alignment. Data are collected and analyzed using Rigaku X-ray system. Samples are prepared for analysis by placing them in an aluminum sample holder that is horizontally rotated at 60 rpm during data acquisition.

FT-IR Spectroscopy
Infrared spectra are acquired on Fourier Transform Infrared Spectrophotometer (FT-IR), a Shimadzu IRPrestige-21, equipped with air cooled high energy ceramic light source, Germanium-coated on potassium bromide (KBr) beamsplitter, a high sensitivity pyroelectric detector (DLATGS) and DRS-8000 diffuse reflectance accessory. Each spectrum represents 40 co-added scans collected at a spectral resolution of 4 $cm^{-1}$. A small amount of the sample is put on the plate (6 mm in diameter and 1.5 mm in depth) of the auto-sampler. A background data set is acquired with a blank sample plate. Reported values are rounded and should therefore be considered approximate.

Differential Scanning Calorimetry (DSC)
DSC analysis is performed using Mettler Toledo DSC822. The sample is placed into an aluminum DSC pan and the weight is accurately recorded. The pan is covered with a lid with a pinhole and then crimped. Each sample is heated under a nitrogen purge at a rate of 5° C./min, up to a final temperature of 220-290° C. Indium metal is used as the calibration standard. Reported values are rounded and should therefore be considered approximate.

High Performance Liquid Chromatography (HPLC) Measurement

HPLC data are obtained by Waters Alliance 2695 HPLC system with 2996 PDA detector using the following conditions;
Column: Inertsil ODS-3 (3 microm, 4.6×150 mm),
Eluent: acetonitrile/10 mM ammonium acetate=32/68,
Detection: UV at 215 nm,
Flow rate: 1 mL/min, and
Column temperature: 40° C.

Data processing is performed with Empower 2 software supplied from Waters Corporation.

Thermogravimetry/Differential Thermal Analysis (TG/DTA)

TG/DTA is performed using Seiko 6200R system. The sample is placed into an aluminum TG/DTA pan. Each sample is heated under a nitrogen purge at a rate of 5° C./min, up to a final temperature of 300° C. Indium metal is used as the calibration standard. Reported values are rounded and should therefore be considered approximate.

Room temperature means 15 to 35° C., but not limited to that as long as the purpose is achieved.

Chemical symbols have their usual meanings throughout the specification; M (mole(s) per liter), L (liter(s)), mL (milliliter(s)), g (gram(s)), mg (milligram(s)), mol (moles), mmol (millimoles), N (normal concentration), n-BuOH (normal butyl alcohol), EtOH (ethyl alcohol), AcOEt (ethyl acetate), MEK (methyl ethyl ketone), THF (tetrahydrofuran), i-PrOH (isopropyl alcohol).

Example 1

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid according to the conventional process A slurry of 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid (1.326 kg, 2.807 mol, a white solid) in ethyl acetate (18.564 L) is dissolved at 70° C. The solution is cooled to 64° C. during 35 min and 200 mg of seed crystal (0.423 mmol) is seeded to the mixture. The mixture is cooled to 40° C. over 5 h period and stirred at this temperature for 14.5 h. The slurry is gradually cooled to 19° C. during 6 h period and the mixture is stirred at this temperature for 46 h. The formed precipitate is collected by filtration and the filter cake is washed with 2.0 L of ethyl acetate. The filter cake is dried under reduced pressure at 50° C. to afford 1.140 kg of the desired crystalline form of 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid (86%).

The symbol "α", "θ", "δ" and "ν" are written as "alpha", "theta", "delta" and "nu", respectively in this specification.

$^1$H-NMR (DMSO-$d_6$) delta: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.19 (2H, d, J=5.9 Hz), 3.75-3.62 (2H, m), 3.48-3.30 (2H, m), 2.90-2.74 (2H, m), 2.50 (2H, s), 2.29-2.13 (2H, m), 1.94-1.23 (9H, m).

A signal due to $CO_2H$ is not observed.

m.p. (DSC onset): 169° C.

The temperature has a margin of error of +/−1° C.

Crystallinity by PXRD: Crystal (FIG. 1): Main peaks at 2-Theta: 5.9, 9.3, 9.8, 11.9, 13.7, 14.3, 15.0, 17.8, 18.2-19.3, 19.7, 22.6, 23.4-24.5 and 24.9 (°). Each peak has a margin of error of +/−0.2.

IR nu (diffuse reflection) (FIG. 6): 4389-4383, 3426, 2943-2937, 2120, 1904, 1724, 1614, 1535, 1508, 1437, 1420, 1287, 1261, 1221, 1180, 1121, 1094, 1059, 1022, 991, 974, 957, 934, 918, 868, 827, 783, 746, 731, 654, 638, 615, 588, 554, 542 and 507 cm$^{-1}$. Each peak has a margin of error of +/−2 cm$^{-1}$. Anal. Calcd for $C_{22}H_{27}N_2O_6F_3$: C, 55.93; H, 5.76; N, 5.93. Found: C, 55.76; H, 5.74; N, 5.85.

Example 2

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid hydrochloride salt (HCl-salt)

4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid (244 mg, 0.516 mmol) is dissolved in n-BuOH (4.5 mL) at 70° C., to which conc. HCl (37 wt %, 35.5 microL, 0.425 mmol) is added. The mixture is stirred at 70° C. overnight, then gradually cooled down to room temperature.

Resulting precipitates are collected by filtration, washed with EtOH and dried in vacuo to give 178 mg (0.350 mmol) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid hydrochloride (HCl-salt) as a whites solid (82% yield).

$^1$H-NMR delta: 7.61 (t, 1H, J=8.4 Hz), 7.27 (d, 1H, J=8.8 Hz), 6.96 (d, 1H, J=8.0 Hz), 4.96 (q, 2H, J=8.5 Hz), 4.35-4.15 (m, 2H), 3.80-3.65 (m, 2H), 3.65-3.30 (m, 4H), 3.41 (s, 2H), 3.25-3.00 (m, 2H), 2.30-2.05 (m, 1H), 2.05-1.85 (m, 4H), 1.85-1.55 (m, 4H).

PXRD (FIG. 2): Main peaks at 2-theta: 5.9, 9.4, 11.1, 11.9, 13.2, 18.2, 18.6, 22.1, 25.2 and 26.5 (°). Each peak has a margin of error of +/−0.2. IR nu (diffuse reflection) (FIG. 7): 4392, 3393, 2953, 2517, 1942, 1705, 1618, 1541, 1508, 1439, 1377, 1288, 1261, 1223, 1155, 1111, 1059, 1040, 1011, 966, 941, 878, 856, 787, 754, 733, 654, 625, 590, 573, 557, 529, 503, and 478 cm$^{-1}$.

Each peak has a margin of error of +/−2 cm$^{-1}$.

m.p. (DSC onset): 232° C.

The temperature has a margin of error of +/−1° C.

Anal. Calcd for $C_{22}H_{28}ClF_3N_2O_6$: C, 51.92; H, 5.55; N, 5.50; F, 11.20; Cl, 6.97. Found: C, 51.92; H, 5.55; N, 5.45; F, 11.11; Cl, 6.98.

Example 3

Preparation of 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid hydrobromide salt (HBr-salt)

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid (351 mg, 0.744 mmol) is dissolved in n-BuOH (14 mL) at 65° C., to which EtOH solution of HBr (0.5M, 1.51 mL, 0.759 mmol) is added. The mixture is stirred at 65° C. overnight, then gradually cooled down to room temperature.

Resulting precipitates are collected by filtration, washed with EtOH and dried in vacuo to give 254 mg (0.459 mmol) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid hydrobromide (HBr-salt) as a white solid (62% yield).

¹H-NMR delta: 7.61 (t, 1H, J=8.1 Hz), 7.27 (d, 1H, J=8.8 Hz), 6.97 (d, 1H, J=8.0 Hz), 4.96 (q, 2H, J=8.8 Hz), 4.40-4.15 (m, 2H), 3.80-3.65 (m, 2H), 3.65-3.30 (m, 4H), 3.43 (s, 2H), 3.30-3.05 (m, 2H), 2.30-2.10 (m, 1H), 2.05-1.85 (m, 4H), 1.85-1.55 (m, 4H).

PXRD (FIG. 3): Main peaks at 2-Theta: 9.4, 13.3, 18.4, 18.7, 22.2, 23.2, 23.8, 24.8, 25.2, 25.9 and 26.6 (°). Each peak has a margin of error of +/−0.2. IR nu (diffuse reflection) (FIG. 8): 4405, 3397, 2941, 2693, 2122, 1942, 1717, 1618, 1545, 1508, 1441, 1410, 1377, 1352, 1287, 1261, 1225, 1157, 1111, 1059, 1040, 1011, 968, 941, 874, 856, 787, 754, 735, 652, 621, 590, 571, 557, 525, 503 and 478 cm⁻¹. Each peak has a margin of error of +/−2 cm⁻¹.

m.p. (DSC onset): 256° C.

The temperature has a margin of error of +/−1° C.

Anal. Calcd for $C_{22}H_{28}BrF_3N_2O_6$: C, 47.75; H, 5.10; N, 5.06; F, 10.30; Br, 14.44.

Found: C, 47.88; H, 5.21; N, 4.98; F, 10.15; Br, 14.13.

Example 4

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid p-toluenesulfonate salt (pTSA-salt)

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid (211 mg, 0.477 mmol) is dissolved in AcOEt (6.33 mL) at 65° C. and to which a solution of p-toluenesulfonic acid monohydrate (85.0 mg, 0.447 mmol) in CH₃CN (1.48 mL) is added. The mixture is stirred at 65° C. for 3 min, then gradually cooled down to room temperature. Resulting precipitates are collected by filtration, washed with AcOEt and dried in vacuo to give 249 mg (0.387 mmol) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid p-toluenesulfonate salt (pTSA-salt) as a white solid (87% yield).

¹H-NMR delta: 7.61 (t, 1H, J=8.2 Hz), 7.47 (d, 2H, J=7.9 Hz), 7.27 (d, 1H, J=8.6 Hz), 7.11 (d, 2H, J=7.9 Hz), 6.96 (d, 1H, J=8.6 Hz), 4.95 (q, 2H, J=8.6 Hz), 4.40-4.15 (m, 2H), 3.80-3.65 (m, 2H), 3.65-3.30 (m, 4H), 3.42 (s, 2H), 3.30-3.05 (m, 2H), 2.28 (s, 3H), 2.40-2.05 (m, 1H), 2.05-1.85 (m, 4H), 1.80-1.55 (m, 4H).

PXRD (FIG. 4): Main peaks at 2-theta: 5.3, 11.9, 14.6, 16.0, 18.5, 18.7, 20.1, 20.6, 21.1, 22.7 and 23.0 (°). Each peak has a margin of error of +/−0.2.

IR nu (diffuse reflection) (FIG. 9): 4438, 4369, 3397, 3017, 2868, 2768 1902, 1701, 1616, 1541, 1508, 1466, 1436, 1422, 1371, 1290, 1267, 1206, 1180, 1150, 1117, 1038, 1013, 972, 918, 881, 860, 847, 812, 783, 738, 708, 677, 650, 611, 565 and 492 cm⁻¹. Each peak has a margin of error of +/−2 cm⁻¹.

m.p. (DSC onset): 207° C.

The temperature has a margin of error of +/−1° C.

Anal. Calcd for $C_{25}H_{35}F_3N_2O_9S$: C, 54.03; H, 5.47; N, 4.35; F, 8.84; S, 4.97.

Found: C, 54.00; H, 5.49; N, 4.39; F, 8.85; S, 4.79.

Example 5

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid hemi-ethanedisulfonate salt (EDSA-salt)

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid (207 mg, 0.438 mmol) is dissolved in AcOEt (6.21 mL) at 65° C. and to which a solution of ethanedisulfonic acid dihydrate (49.6 mg, 0.219 mmol) in EtOH (0.311 mL) is added. The mixture is stirred at 65° C. for 3 min, then gradually cooled down to room temperature. Resulting precipitates are filtered, washed with AcOEt and dried in vacuo to give 223 mg (0.394 mmol) of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid hemi-ethanedisulfonate salt (EDSA-salt) as a white solid (90% yield).

¹H-NMR delta: 7.61 (t, 1H, J=8.2 Hz), 7.27 (d, 1H, J=7.9 Hz), 6.96 (d, 1H, J=8.6 Hz), 4.95 (q, 2H, J=8.6 Hz), 4.40-4.15 (m, 2H), 3.80-3.65 (m, 2H), 3.65-3.30 (m, 4H), 3.39 (s, 2H), 3.25-3.00 (m, 2H), 2.61 (s, 2H), 2.30-2.05 (m, 1H), 2.05-1.85 (m, 4H), 1.80-1.55 (m, 4H).

PXRD (FIG. 5): Main peaks at 2-Theta: 11.3, 13.8, 15.1, 15.9, 18.8, 19.5, 20.2, 20.4, 20.7, 24.0, 24.7 and 26.2 (°). Each peak has a margin of error of +/−0.2.

IR nu (diffuse reflection) (FIG. 10): 4388, 3948, 3422, 2741, 1937, 1717, 1616, 1539, 1506, 1435, 1373, 1285, 1244, 1204, 1169, 1146, 1107, 1030, 989, 972, 951, 901, 854, 789, 772, 756, 741, 729, 652, 615, 546, 532 and 490 cm⁻¹. Each peak has a margin of error of +/−2 cm⁻¹.

m.p. (DSC onset): 246° C.

The temperature has a margin of error of +/−1° C.

Anal. Calcd for $C_{23}H_{30}F_3N_2O_9S$: C, 48.67; H, 5.33; N, 4.94; F, 10.04; S, 5.65.

Found: C, 48.59; H, 5.35; N, 4.94; F, 9.80; S, 5.50.

Example 6

[Hygroscopicity Study]

The salt samples are weighed into aluminum crucibles, placed onto a sample holder, and stored in the humidity chamber at 90% RH (BaCl₂-2H₂O). The samples are visually inspected with a hand magnifying lens and weighed on an analytical balance after five days. The samples are analyzed by PXRD after five days, then allowed to equilibrate at ambient temperatures overnight and re-analyzed by PXRD to evaluate stability of suspected hydrates under ambient conditions.

No deliquescence is observed by visual observations after five days, however, significant weight increases (>15 wt %) are observed for Free form, moderate weight increases (ca. 5 wt %) are observed for the EDSA-salt, while the HCl-salt the HBr-salt and the pTSA-salt show very little weight gain.

No crystal form changes are observed by PXRD after both 5 days and following equilibration at ambient temperature for all four salt samples, however, PXRD pattern of Free form is different from the intact bulk indicating hydrate formation. These results are summarized in Table 1.

TABLE 1

| Salt | Water uptake after 5 days (wt %) | PXRD (compared to intact bulk) | PXRD - overnight at ambient condition |
|---|---|---|---|
| Free form | 16.7 | different | no change |
| pTSA-salt | <0.1 | same | no change |
| HBr-salt | 0.6 | same | no change |
| HCl-salt | 1.1 | same | no change |
| EDSA-salt | 4.8 | same | no change |

Example 7

[Solid-State Stability Study]

Solid-state stability study is performed using Nagano Science Constant temperature/humidity control chamber LH-20-11M or LH-21-11M. The sample is placed in the chamber and exposed under 40° C./75% RH. The crystalline form and thermal behavior of the resultant sample after the exposure are evaluated by PXRD and TG/DTA, respectively. The remaining % and the purity are determined by HPLC measurement.

The remaining % of the HCl-salt, the HBr-salt, the pTSA-salt and the EDSA-salt after storage at 40° C./75% RH for 6 month are 97%, 99%, 98% and 99%, respectively, while the remaining of Free form is 87% (Table 2). In addition, the purity of Free form (95.6%) is obviously lower than these four salts (98.8-100.0%) and a lot of degradation products are observed in Free form. EDSA-salt is the most stable among these four salts.

TABLE 2

Solid-state stability study result under 40° C./75% RH for 6 month

| | Assay | Purity (Area %) | | | | | |
|---|---|---|---|---|---|---|---|
| | Remaining % | Main peak | Degradant | | | | |
| | | | #1 | #2 | #3 | #4 | #5 | #6 |
| Free form | 87 | 95.6 | 1.5 | 0.8 | 1.1 | 0.3 | 0.3 | N.D. |
| HCl-salt | 97 | 98.8 | 0.4 | 0.6 | 0.1 | <0.1 | 0.1 | 0.1 |
| HBr-salt | 99 | 99.9 | N.D. | N.D. | <0.1 | N.D. | <0.1 | <0.1 |
| pTSA-salt | 98 | 99.7 | N.D. | N.D. | 0.3 | N.D. | N.D. | N.D. |
| EDSA-salt | 99 | 100.0 | N.D. | N.D. | N.D. | N.D. | N.D. | N.D. |

Six major degradants of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid are observed after solid-state stability study. # means each degradant.

N.D. means not detected.

Area of the counterion in each salt sample is excluded from the calculation.

Reference 1

General procedure for preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid salts other than the HCl-salt, the HBr-salt, the pTSA-salt and the EDSA-salt:

A solution of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid (approximately 20 mg) in EtOH, n-BuOH, AcOEt, MEK, CH$_3$CN or THF (1.0 mL) is allowed to equilibrate at elevated temperature (65° C. for EtOH, n-BuOH, EtOAc, MEK, and CH$_3$CN, 60° C. for THF) for approximately five minutes before counterion solution is added. The counterion solution in MeOH, EtOH, i-PrOH, dioxane and/or water (1.05 molar equivalents) is added and the resulting mixture is then cooled slowly at 20° C./hour to ambient temperature and allowed to equilibrate overnight. Any precipitate is isolated via vacuum filtration and dried overnight under vacuum at ambient temperature.

Reference 1(a)

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid benzenesulfonic acid salt Trial of salt formation with benzenesulfonic acid is conducted by the general procedure using the said compound in EtOH and benzenesulfonic acid solution in dioxane. The mixture is clear after an addition of the counterion and no solids are observed after cooling. The solution is concentrated by rotavap providing oil and no solids of the salt are obtained.

When CH$_3$CN is used for the trial of salt formation with benzenesulfonic acid instead of EtOH, oil is also provided and no solids of the salt are obtained.

Reference 1(b)

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid p-toluenesulfonic acid salt Trial of salt formation with p-toluenesulfonic acid is conducted by the general procedure using the said compound in EtOH and p-toluenesulfonic acid solution in dioxane. The mixture is clear after an addition of the counterion and no solids are observed after cooling. The solution is concentration by rotavap providing oil and no solids are obtained.

Only oil is obtained. No crystal salt is obtained, according to the general procedure in EtOH. Thus the procedure described in Example 4 is preferable for obtaining the p-toluenesulfonic acid salt for practical use as a pharmaceutical acceptable salt.

Reference 1(c)

Preparation of 4-{[4-({[4-(2,2,2-trifluoroethoxy)-1,2-benzisoxazol-3-yl]oxy}methyl)piperid in-1-yl]methyl}tetrahydro-2H-pyran-4-carboxylic acid zinc salt Trial of salt formation with zinc acetate is conducted by the general procedure using the said compound in EtOH and zinc acetate solution in water. The mixture is clear after an addition of the counterion and no solids are observed after cooling. The solution is concentrated by rotavap providing oil and no solids of the salt are obtained.

Reference 1(d)

Preparation of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid (+)-(1S)-camphor-10-sulfonic acid salt Trial of salt formation with (+)-(1S)-camphor-10-sulfonic acid is conducted by the general procedure using the said compound in EtOH and (+)-(1S)-camphor-10-sulfonic acid solution in EtOH. It affords solids whose PXRD pattern is consistent with the free form of the said compound. Only the free form is recovered.

When AcOEt is used for the trial of salt formation with (+)-(1S)-camphor-10-sulfonic acid instead of EtOH, only the free form is recovered.

Reference 1(e)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
napthalene-2-sulfonic acid salt Trial of salt formation with napthalene-2-sulfonic acid is conducted by the general procedure using the said compound in EtOH and napthalene-2-sulfonic acid solution in EtOH. It affords solids whose PXRD pattern is consistent with the free form of the said compound. Only the free form is recovered.

When AcOEt is used for the trial of salt formation with napthalene-2-sulfonic acid instead of EtOH, only the free form is recovered.

Reference 1(f)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
sodium salt Trial of salt formation with sodium acetate is conducted by the general procedure using the said compound in $CH_3CN$ and sodium acetate solution in MeOH. It affords solids whose PXRD pattern is consistent with the free form of the said compound. Only the free form is recovered.

Reference 1(g)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
betaine salt Trial of salt formation with betaine is conducted by the general procedure using the said compound in MEK and betaine solution in MeOH. It affords solids whose PXRD pattern is consistent with the free form of the said compound. Only the free form is recovered.

Reference 1(h)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
diethylamine salt Trial of salt formation with diethylamine is conducted by the general procedure using the said compound in n-BuOH and diethylamine solution in EtOH. It affords solids whose PXRD pattern is consistent with the free form of the said compound. Only the free form is recovered.

When $CH_3CN$ is used for the trial of salt formation with diethylamine instead of n-BuOH, only the free form is recovered.

Reference 1(i)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid sulfuric acid salt Salt formation with sulfuric acid is conducted by the general procedure using the said compound in n-BuOH and sulfuric acid solution in EtOH. It affords a unique PXRD pattern compared to the free form of the said compound, however, $^1$H-NMR analysis shows 14.0 wt % of n-BuOH, which is consistent with mono-solvates. It is not for practical use as a pharmaceutical acceptable salt.

When MEK is used for salt formation with sulfuric acid instead of n-BuOH, $^1$H-NMR analysis shows 8.5 wt % of EtOH, which is consistent with mono-solvates. It is not for practical use as a pharmaceutical acceptable salt.

Reference 1(j)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
phosphoric acid salt Salt formation with phosphoric acid is conducted by the general procedure using the said compound in n-BuOH and phosphoric acid solution in EtOH. It provides a unique PXRD pattern compared to the free form of the said compound, however, $^1$H-NMR analysis shows 0.1 wt % of EtOH and 0.3 wt % of n-BuOH. It is not for practical use as a pharmaceutical acceptable salt.

When $CH_3CN$ is used for salt formation with sulfuric acid instead of n-BuOH, $^1$H-NMR analysis shows 0.2 wt % of $CH_3CN$. It is not for practical use as a pharmaceutical acceptable salt.

Reference 1(k)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
sodium salt Salt formation with sodium hydroxide is conducted by the general procedure using the said compound in EtOH and sodium hydroxide in EtOH/water. It provides a unique PXRD pattern compared to the free form of the said compound and its $^1$H-NMR spectra shows no significant organic solvent, however, adsorption of more than 40 wt % water after five days at 90% RH is observed in Hygroscopicity study.

When $CH_3CN$ is used for salt formation with sodium hydroxide instead of EtOH, it provides a unique PXRD pattern compared to the free form of the said compound and its $^1$H-NMR spectra is consistent with the structure and shows no significant organic solvent, however, adsorption of more than 40 wt % water after five days at 90% RH is observed in Hygroscopicity study.

Thus the sodium salt is not for practical use as a pharmaceutical acceptable salt.

Reference 1(l)

Preparation of 4-{[4-({[4-(2,2,2-trifluoroethoxy)-1,
2-benzisoxazol-3-yl]oxy}methyl)piperidin-1-yl]
methyl}tetrahydro-2H-pyran-4-carboxylic acid
potassium salt Salt formation with potassium acetate is conducted by the general procedure using the said compound in n-BuOH and potassium acetate solution in MeOH. It provides a unique PXRD pattern compared to the free base of the said compound. The $^1$H-NMR analysis thereof shows no significant residual organic solvent and 0.8 equivalent of acetate present, indicating possible dual salt formation with both potassium and acetate.

When MEK is used for salt formation with potassium acetate instead of n-BuOH, it provides a unique PXRD pattern compared to the free base of the said compound. Its $^1$H-NMR analysis shows no significant residual organic solvent and 0.8 equivalent of acetate present, indicating possible dual salt formation with both potassium and acetate.

In this case the potassium salt is not observed, but potassium acetate salt is observed, which is not for practical use as a pharmaceutical acceptable salt.

Reference 2

[Hygroscopicity Study]

Salts other than the HCl-salt, the HBr-salt, the pTSA-salt and the EDSA-salt, which include salts described in Reference 1(a)-1(l) are not suitable for hygroscopicity study in EXAMPLE 6.

[Solid-State Stability Study]

Salts other than the HCl-salt, the HBr-salt, the pTSA-salt and the EDSA-salt, which include salts described in Reference 1(a)-1(l) are not suitable for Solid-state stability study in EXAMPLE 7.

Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

The invention claimed is:

1. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid HCl-salt, which is characterized by a powder X-ray diffraction (PXRD) pattern obtained by irradiation with Cu-K-alpha radiation which includes main peaks at 5.9, 9.4, 11.1, 11.9, 13.2, 18.2, 18.6, 22.1, 25.2 and 26.5° 2θ, wherein each peak has a margin of error of +/−0.2° 2θ.

2. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid HCl-salt, which is characterized by an infrared (IR) spectrum (diffuse reflection) which shows absorption bands at 4392, 3393, 2953, 2517, 1942, 1705, 1618, 1541, 1508, 1439, 1377, 1288, 1261, 1223, 1155, 1111, 1059, 1040, 1011, 966, 941, 878, 856, 787, 754, 733, 654, 625, 590, 573, 557, 529, 503, and 478 cm$^{-1}$, wherein each peak has a margin of error of +/−2 cm$^{-1}$.

3. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid HCl-salt as described in claim 1, which is further characterized by differential scanning calorimetry (DSC) in which it exhibits an endothermic event at 232° C., wherein the temperature has a margin of error of +/−1° C.

4. A pharmaceutical composition including 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt as described in claim 1, together with one or more pharmaceutically acceptable excipients.

5. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid HBr-salt, which is characterized by a powder X-ray diffraction (PXRD) pattern obtained by irradiation with Cu-K-alpha radiation which includes main peaks at 9.4, 13.3, 18.4, 18.7, 22.2, 23.2, 23.8, 24.8, 25.2, 25.9 and 26.6° 2θ, wherein each peak has a margin of error of +/−0.2° 2θ.

6. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid HBr-salt, which is characterized by an infrared (IR) spectrum (diffuse reflection) which shows absorption bands at 4405, 3397, 2941, 2693, 2122, 1942, 1717, 1618, 1545, 1508, 1441, 1410, 1377, 1352, 1287, 1261, 1225, 1157, 1111, 1059, 1040, 1011, 968, 941, 874, 856, 787, 754, 735, 652, 621, 590, 571, 557, 525, 503 and 478 cm$^{-1}$, wherein each peak has a margin of error of +/−2 cm$^{-1}$.

7. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid HBr-salt as described in claim 5, which is further characterized by differential scanning calorimetry (DSC) in which it exhibits an endothermic event at 256° C., wherein the temperature has a margin of error of +/−1° C.

8. A pharmaceutical composition including 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt as described in claim 5, together with one or more pharmaceutically acceptable excipients.

9. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid pTSA-salt, which is characterized by a powder X-ray diffraction (PXRD) pattern obtained by irradiation with Cu-K-alpha radiation which includes main peaks at 5.3, 11.9, 14.6, 16.0, 18.5, 18.7, 20.1, 20.6, 21.1, 22.7 and 23.0° 2θ, wherein each peak has a margin of error of +/−0.2° 2θ.

10. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid pTSA-salt, which is characterized by an infrared (IR) spectrum (diffuse reflection) which shows absorption bands at 4438, 4369, 3397, 3017, 2868, 2768, 1902, 1701, 1616, 1541, 1508, 1466, 1436, 1422, 1371, 1290, 1267, 1206, 1180, 1150, 1117, 1038, 1013, 972, 918, 881, 860, 847, 812, 783, 738, 708, 677, 650, 611, 565 and 492 cm$^{-1}$, wherein each peak has a margin of error of +/−2 cm$^{-1}$.

11. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid pTSA-salt as described in claim 9, which is further characterized by differential scanning calorimetry (DSC) in which it exhibits an endothermic event at 207° C., wherein the temperature has a margin of error of +/−1° C.

12. A pharmaceutical composition including 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt as described in claim 9, together with one or more pharmaceutically acceptable excipients.

13. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid EDSA-salt, which is characterized by a powder X-ray diffraction (PXRD) pattern obtained by irradiation with Cu-K-alpha radiation which includes main peaks at 11.3, 13.8, 15.1, 15.9, 18.8, 19.5, 20.2, 20.4, 20.7, 24.0, 24.7 and 26.2° 2θ, wherein each peak has a margin of error of +/−0.2° 2θ.

14. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid EDSA-salt, which is characterized by an infrared (IR) spectrum (diffuse reflection) which shows absorption bands at 4388, 3948, 3422, 2741, 1937, 1717, 1616, 1539, 1506, 1435, 1373, 1285, 1244, 1204, 1169, 1146, 1107, 1030, 989, 972, 951, 901, 854, 789, 772, 756, 741, 729, 652, 615, 546, 532 and 490 cm$^{-1}$, wherein each peak has a margin of error of +/−2 cm$^{-1}$.

15. 4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid EDSA-salt as described in claim 13, which is further characterized by differential scanning calorimetry (DSC) in which it exhibits an endothermic event at 246° C., wherein the temperature has a margin of error of +/−1° C.

16. A pharmaceutical composition including 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt as described in claim 13, together with one or more pharmaceutically acceptable excipients.

17. A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HCl-salt as described in claim 1, comprising the step of mixing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid with HCl.

18. A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid HBr-salt as described in claim 5, comprising the step of mixing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid with HBr.

19. A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid pTSA-salt as described in claim 9, comprising the step of mixing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid with p-toluenesulfonic acid.

20. A process for preparing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid EDSA-salt as described in claim 13, comprising the step of mixing 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid with ethanedisulfonic acid.

* * * * *